US00RE35524E

United States Patent [19]

Saulnier et al.

[11] E Patent Number: Re. 35,524

[45] Reissued Date of Patent: Jun. 3, 1997

[54] EPIPODOPHYLLOTOXIN GLUCOSIDE 4'-PHOSPHATE DERIVATIVES

[75] Inventors: Mark G. Saulnier, Middletown, Conn.; Peter D. Senter, Northeast Seattle, Wash.; John F. Kadow, Wallingford, Conn.

[73] Assignee: Bristol-Myers Squibb Company, New York, N.Y.

[21] Appl. No.: 229,659

[22] Filed: Apr. 19, 1994

Related U.S. Patent Documents

Reissue of:

[64] Patent No.: 4,904,768
Issued: Feb. 27, 1990
Appl. No.: 199,731
Filed: May 27, 1988

U.S. Applications:

[63] Continuation-in-part of Ser. No. 81,492, Aug. 4, 1987, abandoned.

[51] Int. Cl.[6] ..... C07H 11/04; C07H 15/00

[52] U.S. Cl. ..... 536/17.1; 536/4.1; 536/17.2; 536/18.1; 536/18.2; 536/18.5; 536/117; 536/124

[58] Field of Search ..... 536/4.1, 18.1, 536/17.2, 18.2, 18.5, 17.1, 117, 124; 514/33, 34, 35, 908

[56] References Cited

U.S. PATENT DOCUMENTS

| | | | |
|---|---|---|---|
| 3,408,441 | 10/1968 | von Wartburg et al. | 536/18.1 |
| 3,524,844 | 8/1970 | Keller-Juslen et al. | 536/18.1 |
| 3,773,803 | 11/1973 | Villax | 260/397.45 |
| 4,185,111 | 1/1980 | Ducep et al. | 424/283 |
| 4,564,675 | 1/1986 | Kurabayashi et al. | 536/18.1 |
| 4,567,253 | 1/1986 | Durst et al. | 536/18.1 |
| 4,687,762 | 8/1987 | Fukushima et al. | 514/34 |
| 4,818,752 | 4/1989 | Williams et al. | 514/54 |
| 4,833,131 | 5/1989 | Williams et al. | 514/54 |
| 4,874,851 | 10/1989 | Vyas et al. | 536/17.2 |
| 4,916,217 | 4/1990 | Saulnier | 536/17.1 |

FOREIGN PATENT DOCUMENTS

| | | |
|---|---|---|
| 0111058 | 6/1984 | European Pat. Off. . |
| 0162701 | 11/1985 | European Pat. Off. . |
| 0226202 | 6/1987 | European Pat. Off. . |
| 1643521 | 4/1971 | Germany . |
| 63-192793 | 8/1988 | Japan . |
| 192793 | 8/1988 | Japan . |
| 514578 | 10/1971 | Switzerland . |
| 543502 | 10/1973 | Switzerland . |
| 589668 | 5/1977 | Switzerland . |

OTHER PUBLICATIONS

Varia, et al. "Phenytoin Prodrugs III: Water-Soluble Prodrugs for Oral and/or Parenteral Use", J. Pharm. Sci., 73 (1984) 1068–73.

Varia, et al. "Phenytoin Prodrugs IV: Hydrolysis of Various 3-(Hydroxymethyl), Phenytoin Esters," J. Pharm. Sci. 73, 1074 (1984).

Varia, et al. "Phenytoin Prodrugs V: In Vivo Evaluation of Some Water Soluble Phenytoin Prodrugs in Dogs," J. Pharm. Sci. 73, 1080 (1984).

Ball, C.R., et al., "Enzyme Activated Alkylating Agents," J. Brit. J. Cancer, 1973, 78, 81.

Harper, N.J., "Drug Latentiation," *J. Med. Pharm. Chem.*, 1959, 1, 467, 470–71.

Chem. Abstr. 96: 218193μ (1982).

Rosowsky, et al., J. Med. Chem. 25, 171–78 (1982).

Godfroid, et al., "Structure Activity Relationship in PAF-Acether 3", J. Med. Chem. 1987, 30, 792–97.

Toyama Chemical KK SP 102362 (86–2406 C115).

Burger's Medicinal Chemistry, 4th Ed., 1979, 640–41.

Chem. Abstr. 104:199672q (1986).

E.K. Ryu, et al., "Phospholipid-Nucleoside Conjugates", J. Med. Chem., 25, 1322–29 (1982).

Japanese Patents Gazette, Week 8740, Nov. 18, 1987 p. 10, JP-034964 and JP-037-232.

Melby, J.C., et al., "Comparative studies on Absorption and Metabolic Disposal of Water Soluble Steroids," 1961, pp. 75–82.

Kauffman, et al., "Absorption and excretion of clindamycin-2-phosphate in children after intramuscular injection", Clin.Pharm.Thera., 13 (1972) 704–9.

E. Müller, Methoden der Organischen Chemie, 4th Ed. (1964) 162–163, 212–215, 324–329, 406–07, 457–61 (w/translation).

Merck Index, 10th Ed. (1983), Camptothecin (No. 1714) Etoposide (No.3832) Doxorubicin (No. 3435) Teniposide (No. 8978).

Bukhari, M.A., et al., Aryl-2-Halogenoalkylamines—XXVI, Biochem. Pharmacol., 1972, 21, 963–67.

Keller-Juslen, C., et al., "Synthesis and Antimitotic Activity of Glycosidic Lignan Derivatives Related to Podophyllotoxin", J. Med. Chem., 1971, 14, 936–940.

Chem. Abstracts: 96:96837j (1982).

Chem. Abstracts: 109:23200y (1988).

Chem. Abstracts: 70:78340a (1969).

Chem. Abstracts: 73:118783t (1970).

H. Staehlin, "Chemie und Wirkungsmechanismus von Podophyllin-Derivaten", Planta Medica, 1972, 22(3), 336–47 (w/translation).

Arnold, A.M., et al., "Etosposide: A New Anti-Cancer Agent", The Lancet, 2, pp. 912–914 (1981).

Zent Molekularbiol DD-222-595-A, Jan. 24, 1984.

A. Sinkula, et al., "Rationale for Design of Biologically Reversible Drug Derivatives: Pro Drugs", J. Pharm. Sci., 1975, 64, pp. 181–210.

A. Seligman, et al., "Design of Spindle Poisons Activated Specifically by Prostatic Acid Phosphatase (PAP) and New Methods for PAP Cytochemistry" Cancer Chemother. Rep. 59: 233–242, 1975.

Cancer Chemotherapy Reports Part I (1975) 59:233–242.

*Primary Examiner*—John Kight, III
*Assistant Examiner*—Everett White
*Attorney, Agent, or Firm*—Mollie M. Yang; Samuel J. DuBoff

[57] ABSTRACT

Phosphate derivatives of 4'-demethylepipodophyllotoxin glucosides are novel antitumor agents and the salts thereof offer the pharmaceutical advantage of high water solubility.

29 Claims, No Drawings

EPIPODOPHYLLOTOXIN GLUCOSIDE 4'-PHOSPHATE DERIVATIVES

Matter enclosed in heavy brackets [ ] appears in the original patent but forms no part of this reissue specification; matter printed in italics indicates the additions made by reissue.

This application is a continuation-in-part of U.S. patent application, Ser. No. 081,492, filed on Aug. 4, 1987 in the United States Patent and Trademark Office, now abandoned.

BACKGROUND OF THE INVENTION

I. Field of the Invention

The present invention relates to 4'-phosphate derivatives of epipodophyllotoxin glucosides, to their antitumor use, and to pharmaceutical compositions containing these new agents.

II. Description of the Prior Art

Etoposide (VP-16, I) and teniposide (VM-26, II) are clinically useful anticancer agents derived from the naturally occurring lignan, podophyllotoxin (III); the class of compounds including etoposide and teniposide is sometimes referred to as 4'-demethylepipodophyllotoxin glucosides. Etoposide and teniposide are active in the treatment of a variety of cancers including testicular, small cell lung, ovarian, breast, thyroid, bladder, brain, non-lymphocytic leukemia, and Hodgkin's disease.

Compounds I and II, and the method for producing them are disclosed in U.S. Pat. No. 3,408,441 to Wartburg et al. and U.S. Pat. No. 3,524,844 to Keller-Juslen et al. The compounds disclosed therein, in particular etoposide and teniposide, serve as starting material for our preparation of epipodophyllotoxin glucoside 4'-phosphate derivatives of the present invention.

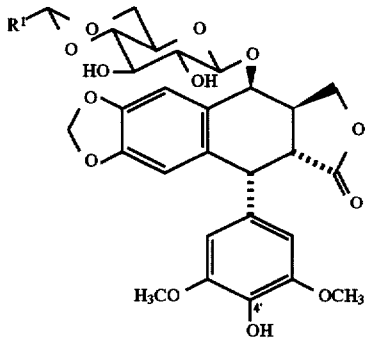

I $R^1 = CH_3$
II $R^1$ = 2-thienyl

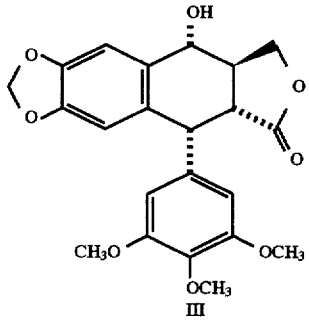

III

Phosphorylation of therapeutic agents containing a hydroxyl group has been used as a means for drug latentiation; the phosphorylated derivatives may then be cleaved in vivo by a phosphatase to liberate the active parent molecule. A brief discussion of phosphates as potential prodrugs is included in the review article entitled "Rational for Design of Biologically Reversible Drug Derivatives: Prodrugs" (Sinkula and Yalkowsky, J. pharm. Sci., 1975, 64: 181–210 at 189–191). Examples of phosphates of known antitumor agents include camptothecin (Japan Kokai 21-95,394 and 21-95,393, Derwent Abst. No. 87-281016 and 87-281015, respectively) and daurorubicin (U.S. Pat. No. 4,185,111).

Podophyllotoxin phosphate disodium salt IV was prepared by Seligman et al. However, the phosphate was not hydrolyzed by prostatic acid phosphatase and did not show reduced toxicity over the parent podophyllotoxin (Cancer Chemotherapy reports Part I, 1975, 59: 233–242).

IV

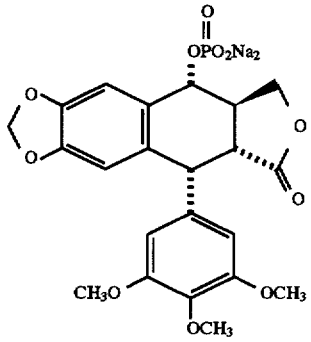

The present invention provides phosphate esters of 4'-demethylepipodophyllotoxin glucosides which are active antitumor agents. In particular, the dihydrogen phosphate of 4'-demethylepipodophyllotoxin glucosides and salts thereof are highly water-soluble thus providing a superior pharmaceutical advantage over the current therapeutic agents of this class, etoposide and teniposide, which have minimal water solubility.

SUMMARY OF THE INVENTION

The present invention provides 4'-phosphate derivatives of 4'-demethylepipodophyllotoxin glucosides of general formula V, and pharmaceutically acceptable salts thereof

V

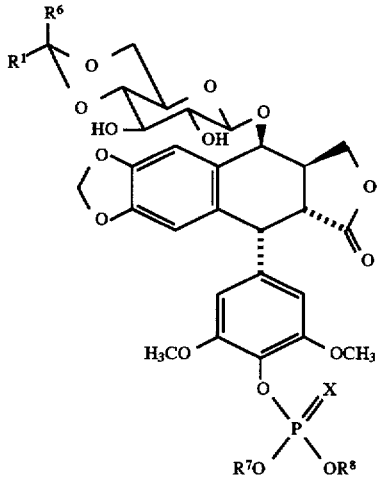

wherein $R^6$ is H and $R^1$ is selected from the group consisting of $(C_{1-10})$alkyl; $(C_{2-10})$alkenyl; $(C_{5-6})$ cycloalkyl; 2-furyl; 2-thienyl; $(C_{6-10})$aryl; $(C_{7-14})$aralkyl; and $C_{8-14}$) aralkenyl wherein each of the aromatic rings may be unsubstituted or substituted with one or more groups selected from halo, $(C_{1-8})$alkyl, $(C_{1-8})$alkoxy, hydroxy, nitro, and amino; or $R^1$ and $R^6$ are each $(C_{1-8})$alkyl; or $R^1$ and $R^6$ and the carbon to which they are attached join to form a $(C_{5-6})$ cycloalkyl group; X is oxygen or sulfur; $R^7$ and $R^8$ are independently selected from the group consisting of H, $(C_{1-5})$ alkyl, A-substituted $(C_{1-5})$ alkyl, $(C_{3-6})$cycloalkyl, A-substituted $(C_{3-6})$cycloalkyl, $(C_{6-10})$aryl, A-substituted aryl, alkyl-substituted aryl, $(C_{7-14})$aralkyl, A-substituted aralkyl, and alkyl-substituted aralkyl; wherein said A-substituents are one or more groups selected from hydroxy, alkoxy, alkanoyloxy, cyano, amino, alkylamino, dialkylamino, carboxy, alkylthio, mercapto, mercaptothio, nitropyridyl disulfide, alkanoylamino, alkanoyl, carbamoyl, nitro, and halo.

The salts of compound V include both the monoanionic and the dianionic salts. The cation may be a metal ion such as one from the alkali metal or alkaline earth metal groups or other common metal ions; or an organic nitrogen-containing group such as ammonium, mono-, di-, or trialkylammonium, or pyridinium. The cation is preferably selected from the group consisting of sodium, potassium, lithium, cesium, magnesium, calcium, aluminum, ammonium and mono-, di-, and trialkylammonium. A preferred embodiment provides compounds of formula V wherein $R^7$ and $R^8$ are both H, and pharmaceutically acceptable salts thereof. A most preferred embodiment provides etoposide 4'-dihydrogen phosphate and thiophosphate, and their respective disodium salts VIa and VIb. A further preferred embodiment provides

VI

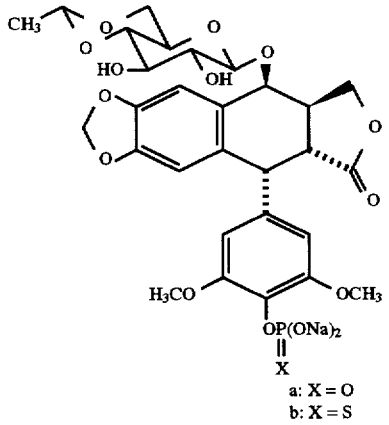

compounds of formula V wherein $R^7$ and $R^8$ are the same and are selected from the group consisting of 2,2,2-trihaloethyl, 2-cyanoethyl, $(C_{1-5})$alkyl, phenyl, and phenylalkyl, wherein the phenyl ring is optionally substituted with alkyl, halogen, or nitro.

A further aspect of this invention provides antitumor phosphoroamidate derivatives of formula VII and pharmaceutically acceptable salts thereof,

VII

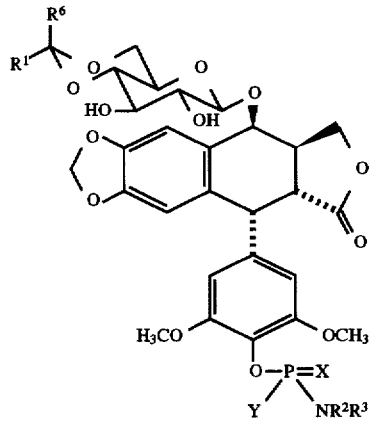

wherein $R^1$, $R^6$, and X are as previously defined; Y is Cl, OH, or $NR^4R^5$; $R^2$, $R^3$, $R^4$, and $R^5$ are each independently selected from the group consisting of H, $(C_{1-5})$ alkyl, $(C_{2-5})$ alkenyl, $(C_{3-6})$ cycloalkyl, A-substituted $(C_{1-5})$ alkyl, A-substituted $(C_{2-5})$ alkenyl, A-substituted $(C_{3-6})$ cycloalkyl; or $R^2$, $R^3$, and the nitrogen to which they are attached together represent to 3- to 6-membered ring; or $R^4$, $R^5$, and the nitrogen to which they are attached together represent a 3- to 6-membered ring; wherein said A-substituents are as previously defined.

Another aspect of the present invention provides dichlorophosphate intermediates of formula VIII wherein $R^1$, $R^6$ and X are as previously defined; these agents are useful in the preparation of compounds of formula V.

VIII

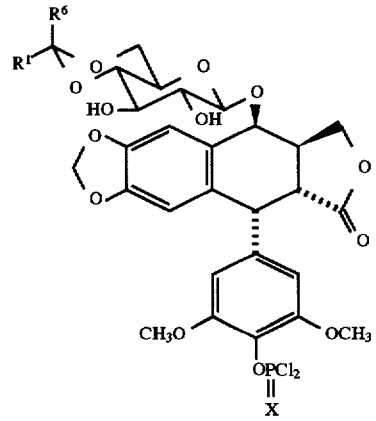

Yet a further aspect of the present invention provides a process for preparing a compound of formula V wherein $R^7$ and $R^8$ are both H and its pharmaceutically acceptable salts, which comprises the steps of (a) converting a compound of formula IX

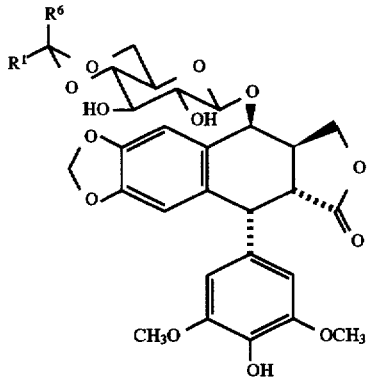

IX into a compound of formula X wherein $R^1$, $R^6$, and X are as previously defined and G is a phosphate protecting group; (b) removing the phosphate protecting group; and (c)

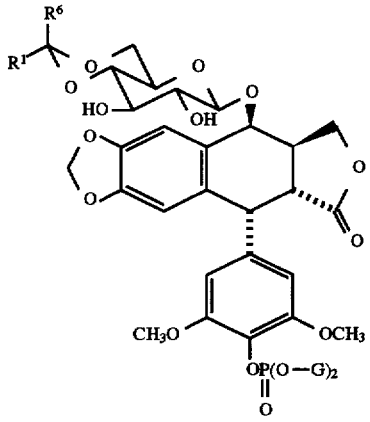

X optionally converting the product of step (b) to a pharmaceutically acceptable salt. Phosphate protecting groups include, but are not limited to, those within the definition of $R^7$ given above except H.

DETAILED DESCRIPTION OF THE INVENTION

As used herein, unless otherwise specied, the term "alkyl" means straight or branched carbon chains; "halo" includes bromo, chloro, fluoro, and iodo; "etopofos" is the compound etoposide 4'-phosphate disodium salt.

The phenol group of 4'-demethylepipodophyllotoxin glucosides may be phosphorylated with phosphorous oxychloride and thiophosphoryl chloride to give the corresponding dichlorophosphate and dichlorothiophosphate, respectively (formula VIII). The phosphorylation reaction is performed in a suitable anhydrous organic solvent, for example acetonitrile, and preferably in the presence of a tertiary amine base, for example N,N-diisopropylethylamine. The course of the reaction may be monitored by thin layer chromatography (TLC) by which the optimum reaction time may be judged by the appearance of product or the disappearance of the starting material, or both. In our experience, the reaction period may take from about 4 hours to about 72 hours. The length of reaction time required appears to be related to the quality of the phosphorous reagent used.

The 4'-dichlorophosphates of formula VIII are versatile intermediates which may subsequently react with nucleoophiles to provide a variety of phosphate and thiophosphate derivatives. Thus the intermediates may be hydrolyzed to provide the phosphates, and in the presence of a base the phosphate salts are obtained. For example, VIII treated with an excess of aqueous sodium bicarbonate solution provides the corresponding 4'-phosphate disodium and 4'-thiophosphate disodium salts; bicarbonates of other cations such as potassium and ammonium may also be used to provide the respective salts. The dichlorophosphate intermediate VIII may react with amines to afford either the corresponding phosphorodiamidate or the chlorophosphoromonoamidate. Examples of suitable amines include, but are not limited to, ammonia, primary amines such as ethylamine, chloroethylamine, allylamine, dimethylaminopropylamine, hydroxyethylamine, cyclohexylamine, and aminocyclohexanol; and secondary amines such as diethylamine, piperidine, ethylmethylamine, methylaminoethanol, ethylbutylamine, and the like. The amount of the amine used relative to that of the epidpodophyllotoxin dichlorophosphate may be adjusted so as to favor one or the other reaction product. For example, when a large excess of the amine relative to the epipodophyllotoxin is used, the symmetrical phosphorodiamidate is obtained, i.e. compounds of formula VII wherein Y is the same as $NR^2R^3$; the chlorophosphoromonoamidate, i.e. compounds of formula VII wherein Y is Cl, may be prepared when a more controlled amount of the amine is used. The chlorophosphoromonoamidate may be hydrolyzed to provide compounds of formula VII wherein Y is OH or its salts, or it may react further with a second amine to provide the unsymmetrical phosphorodiamidate, i.e. compounds of formula VII wherein Y is $NR^4R^5$ and is different from $NR^2R^3$.

The above-described procedure is illustrated in the following reaction scheme.

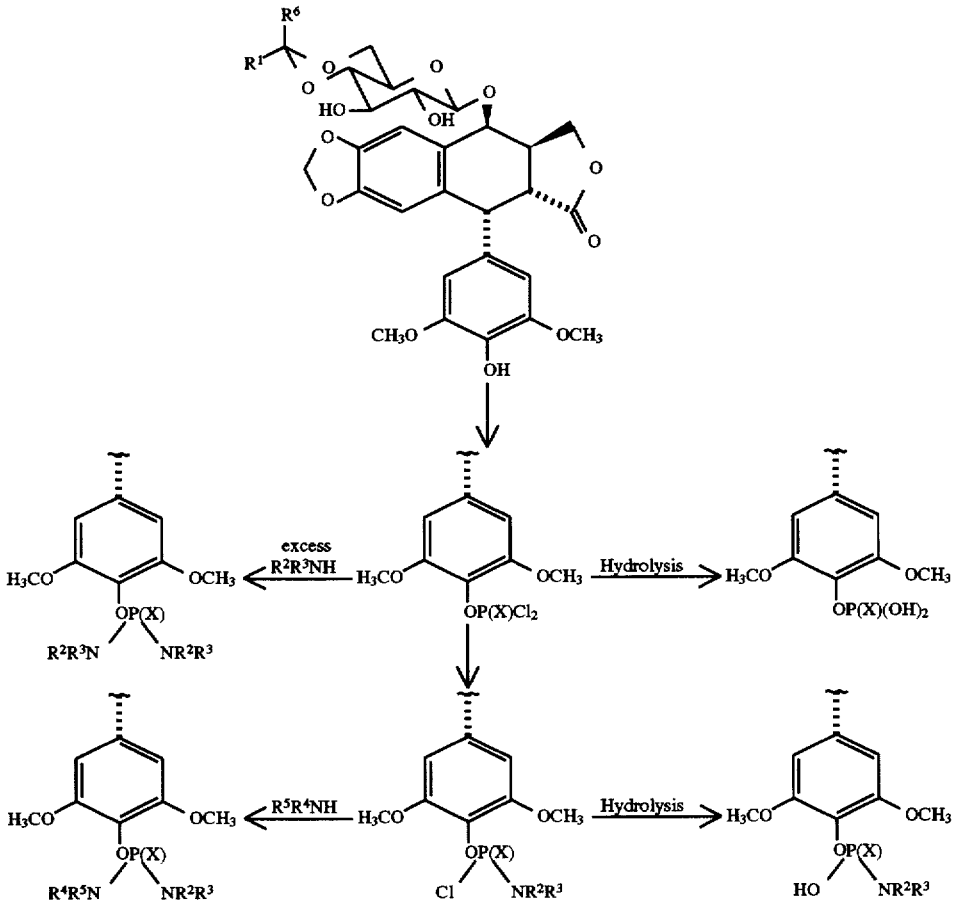

Phosphate triesters are compounds of formula V wherein $R^7$ and $R^8$ are not H, and they may be prepared by treating a 4'-demethylepipodophyllotoxin glucoside with a halophosphate diester, [i.e. Hal-P(X)($OR^7$) ($OR^8$)]. It has been found that this reaction is most efficiently performed in acetonitrile in the presence of an organic trialkylamine base; the preferred base is diisopropylethylamine. At least one equivalent of the halophosphate and the amine base is used, but both reagents are preferably employed in molar equivalents in slight excess relative to that of the epipodophyllotoxin glucoside reactant. The reaction may be carried out at any temperature conductive to product formation; however, slightly elevated temperatures, e.g. 30°–40° C. appear to facilitate the reaction which may take up to several days to go to completion. Symmetrical halophosphate diesters [i.e. $R^7=R^8$] may be conventionally prepared from the alcohol and e.g. phosphoryl chloride, and unsymmetrical ones [i.e. $R^7 \neq R^8$] may be prepared from the alcohol and dihalophosphate ester. It is also possible to prepare phosphate triesters by other routes, for example by first converting the phenol into a phosphite ester, e.g. by reacting with a reagent such as $(PhCH_2O)_2PN(i\text{-}pr)_2$, and subsequently oxidizing the phosphate to the phosphate ester using e.g. m-chloro perbenzoic acid.

Phosphate triesters may additionally serve as intermediates in the preparation of compounds of formula V and salts thereof. Thus, for example, the dihydroxy phosphate (V, $R^7=R^8=H$) is obtained when the diphenyl ester (V, $R^7=R^8=$ phenyl) is subjected to catalytic hydrogenation. Other suitable phosphate protecting groups include but are not limited to, 2,2,2-trichloroethyl, benzyl, cyanoethyl, p-nitro substituted phenyl, benzyl, phenethyl, and p-bromophenyl. The dihydroxy phosphate (V, $R^7=R^8=H$) are converted to base salts by reacting with the appropriate base, e.g. sodium bicarbonate, ammonium bicarbonate or organic amines. Alternatively, the salts may also be generated by eluting the dihydroxy phosphate through a column of an exchange resin containing the desired cation.

Although the present invention utilizes phosphorous oxychloride, halophosphate diesters, and their respective sulfur analogs as the phosphorylating reagent, it is to be understood that other phosphorous reagents capable of phosphorylating phenols may also be used, and appropriate reaction conditions and medium may be chosen according to the phosphorylating agent selected. The review article entitled "Current Methods of Phosphorylation of Biological Molecules" (Synthesis, 1977, 737–52) contains further examples of phosphorylating agents and is hereby incorporated by reference.

BIOLOGICAL PROPERTIES

Representative compounds of the present invention were evaluated for antitumor activity against transplantable murine P388 leukemia. In all experiments female $CDF_1$ mice implanted with a tumor inoculum of $10^6$ ascites cells of P388 murine leukemia were used. In experiments using etoposide 4'-phosphate, its disodium salt, and etoposide 4'-thiophosphate disodium salt, tumor implantation and drug treatment were both via the iv route. In all other experiments tumor implant and drug treatment were via the ip route. In all cases, however, the positive control, etoposide, was administered ip. The experiments lasted 28 to 46 days at the end of which time the number of survivors was noted. Antitumor activity is expressed as % T/C which is the ratio of the median survival time (MST) of drug-treated group to the MST of saline-treated control group. A compound having % T/C value of 125 or greater is generally considered to have significant antitumor activity in the P388 test. Table I presents the results of the above-described evaluation; the maximum % T/C values and doses giving that effect are reported.

TABLE I

Antitumor Activity Against Muring P388 Leukemia.

| Compound of | Dose* (mg/kg/inj) | Route | MST(d) | % T/C |
|---|---|---|---|---|
| TUMOR CELLS IMPLANTED INTRAVENOUSLY | | | | |
| Example 1 | 140 | IV | 29.0 | 363 |
| (Etoposide) | 50 | IP | 20.5 | 256 |
| Example 4 | 200 | IP | 18.0 | 225 |
| (Etoposide) | 100 | IP | 21.5 | 269 |
| Example 8 | 125 | IV | 24.5 | 306 |
| (Etoposide) | 100 | IP | 29.5 | 369 |
| TUMOR CELLS IMPLANTED INTRAPERITONEALLY | | | | |
| Example 2 | 240 | IP | 16.5 | 165 |
| (Etoposide) | 60 | IP | 25.0 | 250 |
| Example 3 | 200 | IP | 15.5 | 155 |
| (Etoposide) | 100 | IP | 27.0 | 270 |
| Compound of | (mg/kg/inj) | Route | MST(d) | Dose* % T/C |
| Example 7 | 240 | IP | 25.0 | 250 |
| (Etoposide) | 100 | IP | 26.0 | 260 |
| Example 9 | 150 | IP | 19.5 | 217 |
| (Etoposide) | 100 | IP | 24.0 | 267 |

*Drugs were administered on day 5 and 8 unless otherwise specified (day 1 being the day of tumor implantation).

The antitumor compounds of the present invention have been demonstrated to be active against transplanted tumors in experimental animals. Specifically, the compound represented by formula VIa ("etopofos") shows significantly higher antitumor activity than etoposide in the P388 test. This selective agent represents a highly water soluble prodrug of etoposide which has reduced antitumor activity in-vitro and is rapidly cleaved by alkaline phosphatase resulting in the release of etoposide. The etoposide that is released exhibits identical cytotoxicity to the parent drug.

Accordingly, the present invention provides a method for inhibiting mammalian tumors which comprises administering an effective tumor-inhibiting dose of an antitumor compound of formula V or VII to a tumor bearing host. For this purpose, the drug may be administered by conventional routes including, but not limited to, intravenous, intramuscular, intratumoral, intraarterial, intralymphatic, and oral.

A further aspect of the present invention provides a pharmaceutical composition which comprises a compound of formula V or VII and a pharmaceutically acceptable carrier. The antitumor composition may be made of any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiological saline or some other sterile injectable medium immediately before use.

Optimal dosages and regimens for a given mammalian host can be readily ascertained by those skilled in the art. It will, of course, be appreciated that the actual dose used will vary according to the particular composition formulated, the particular compound used, the mode of application and the particular site, host and disease being treated. Many factors that modify the action of the drug will be taken into account including age, weight, sex, diet, time of administration, route of administration, rate of excretion,, condition of the patient, drug combinations, reactions sensitivities and severity of the disease.

The following examples are for illustrative purposes only and should not be construed as limiting the scope of the invention which is defined solely by the claims appended to this application.

In the following examples, proton and carbon nuclear magnetic resonance (NMR) spectra (using $CDCl_3$ or $D_2O$ as an internal reference) and phosphorous NMR spectra (using 85% aqueous $H_3PO_4$ as an external reference) were recorded on a Bruker WM360 spectrometer. Infrared spectra (IR) were determined on a Perkin-Elmer 1800 Fourier Transform Infrared Spectrophotometer. "Flash chromatography" refers to the method described by Still (Still, W. C.; Kahn, M.; Mitra, A.; J. Org. Chem., 1978 43, 2923) and was carried out using E. Merck silica gel (230–400 mesh). Reverse phase chromatography was carried out under a positive nitrogen pressure using C18 (Octadecylsilane) bonded to silica gel (40-μm diameter, J. T. Baker supplier).

EXAMPLE 1

Etoposide 4'-Phosphate Disodium Salt (Compound VIa)

A magnetically stirred suspension of etoposide (2.30 g, 3.91 mmol) in dry acetonitrile (210 ml) was warmed to give a nearly complete solution. The solution was allowed to cool to room temperature, and N,N-diisopropylethylamine (2.36 ml, 13.5 mmol) was added. The mixture was then cooled to 0° C. and $POCl_3$ (666 mg, 4.34 mmol) was added via syringe over 30 seconds. The mixture was allowed to slowly come to room temperature over 2–3 hours and stirring continued at room temperature for 63 hours. At the end of this period 20% by volume was removed and treated with diethylamine as described in Example 2. The remainder was treated with a solution of sodium bicarbonate (6.0 g, 71.4 mmol) in deionized $H_2O$ (110 ml), the mixture was stirred at room temperature for 80 minutes, and then partitioned with saturated aqueous sodium bicarbonate (20 ml) deionized $H_2O$ (125 ml), and ethyl acetate (350 ml). The organic layer was further extracted with deionized $H_2O$ (1×50 ml) and the combined aqueous layers were washed with ethyl acetate (250 ml) and then subjected to a vacuum of 0.5 mm at room temperature for 1 hour to remove dissolved solvents. The aqueous portion was then applied to a 4 cm diameter column containing 15 cm of octadecylsilane bonded to silica gel which had been packed in methanol and equilibrated with $H_2O$. After all of the aqueous portion was applied, the column was eluted with $H_2O$ (175 ml) to remove inorganic salts and then 4:1 $H_2O$:$CH_3OH$ eluted the product. Concentration of the solvent at 0.5 torr provided 744 mg (36%) of the pure title compound as a colorless solid. Alternatively lyophilization provides the pure title compound as a very fluffy low density solid.

IR (KBr) 3426, 1775, 1593, 1505, 1486, 1337, 1239, 1191, 1122, 1078, 1034, 983, 927, 888, 876, 851, 840, 697, 684, 664, 547 $cm^{-1}$.

360 MHz $^1H$ NMR ($D_2O$) δ6.93 (s, 1H), 6.59 (s, 1H), 6.27 (s, 2H), 5.93 (d, 2H), 5.09 (d, 1H, J=2.8 Hz), 4.83 (q, 1H, J=5.0 Hz), 4.68 (d, 1H, J=7.9 Hz), 4.62 (d, 1H, J=5.7 Hz), 4.47 –4.35 (m, 2H), 4.24 (dd, 1H, J=4.4 and 10.4 Hz), 3.64 (s, 6H), 3.68–3.52 (m, 3H), 3.44–3.30 (m, 3H), 3.17–3.07 (m, 1H), 1.31 (d, 3H, J=5.0 Hz).

90 MHz $^{13}C$ NMR ($D_2O$) δ178.5, 151.8, 148.1, 146.1, 135.0, 132.6, 130.9, 127.4, 109.9, 109.5, 107.4, 101.3 100.4, 99.6, 79.2, 73.7, 72.7, 72.2, 69.1, 67.1, 65.4, 55.6, 42.8, 40.3, 37.5, 18.8.

146 MHz $^{31}P$ NMR ($D_2O$) δ3.79.

Mass spectrum (FAB), m/e, 713 ($M^+$+H). $C_{29}H_{31}Na_2O_{16}P$ requires $M^+$, 712.

Anal. Calcd. for $C_{29}H_{31}Na_2O_{16}P$: C, 48.89; H, 4.39; Na, 6.45. Found*: C, 48.72; H, 4.56; Na, 6.56.

*Adjusted for 8.16% $H_2O$ determined by Karl Fischer analysis.

EXAMPLE 2

Etoposide 4'-(Bis-[N,N-diethyl]phosphonamide) (VII, X=O, $R^1$=methyl, $R^6$=H, Y=$N(Et)_2$, $R^2$ =$R^3$=Et)

As indicated in Example 1, 20% by volume of the reaction product mixture of etoposide and $POCl_3$ was added to diethylamine (4 mL) and stirred at room temperature for 3 hours. The solvent was evaporated in vacuo and the light orange residue purified by flash chromatography on silica gel. Elution with 4% methanol in methylene chloride provided 271.3 mg (46.9%) of the pure title compound as a light yellow solid.

IR (KRr) 3408, 2974, 2936, 2877, 1774, 1598, 1508, 1486, 1467, 1421, 1383, 1339, 1234, 1191, 1162, 1130, 1098, 1079, 1037, 902, 858, 795, 713, 700, 544 $cm^{-1}$.

360 MHz $^1H$ NMR ($CDCl_3$) δ6.79, (s, 1H), 6.50 (s, 1H), 6.20 (s, 2H), 5.96 (ABq, 2H), 4.87 (d, 1H, J=3.2 Hz), 4.71 (q, 1H, J=5.1 Hz), 4.61 (d, 1H, J=7.6 Hz), 4.57 (d, 1H, J=5.2 Hz), 4.39 (dd, 1H, J=9.1 and 10.2 Hz), 4.22–4.13 (m, 2H), 3.74 (m, 1H), 3.65 (s, 6H), 3.55 (m, 1H), 3.40 (m, 1H), 3.32–3.10 (m, 11H), 2.94–2.83 (m, 1H), 1.37 (d, 3H, J=5.1 Hz), 1.10 (m, 12H).

146 MHz $^{31}P$ NMR ($CDCl_3$) δ16.49.

Mass spectrum (FAB), m/e, 779 ($M^+$+H), 573 ($M^+$–sugar). $C_{37}H_{51}N_2O_{14}P$ requires $M^+$, 778.

EXAMPLE 3

Etoposide 4'-(N,N-[2-chloroethyl]phosphoryl chloride) (VII, $R^1$=methyl, $R^6$=H, X=O, Y=Cl, $R^2$= $R^3$=$CH_2CH_2Cl$)

A magnetically stirred suspension of etoposide (2.00 g, 3.40 mmol) in dry acetonitrile (220 mL), was warmed to give a nearly complete solution. The mixture was cooled to room temperature and treated with N,N-diisopropylethylamine (2.05 mL, 11.8 mmol). The mixture was then cooled to 0° C. under $N_2$ and phosphorous oxychloride (624 mg, 4.07 mmol) added by syringe over 30 seconds. The mixture was magnetically stirred at 0° C. for 2.5 hours and then at room temperature for an additional 1.5 hours. Bis-(2-chloroethylamine) hydrochloride (1.82 g, 10.2 mmol) was then rapidly added followed immediately by additional N,N-diisopropylethylamine (2.10 mL, 12.0 mmol). The mixture was stirred at room temperature for 85 minutes, concentrated in vacuo to a volume of about 5 mL, and dissolved in ethyl acetate (400 mL) and methanol (5 mL). The resulting solution was washed with pH 5 buffer (2×200 mL), water (150 mL), and brine (150 mL) and dried over $Na_2SO4/MgSO4$. Evaporation of the solvent gave a yellow orange solid which was purified by flash chromatography on silica gel with 3–4% methanol in methylene chloride to provide 1.25 g (45.4%) of the pure title compound as a colorless solid.

360 MHz $^1H$ NMR ($CDCl_3$) δ6.82 (s, 1H), 6.52 (s, 1H), 6.27 (s, 2H), 5.99 (d, 2H), 4.90 (d, 1H, J=3.4 Hz), 4.73 (q, 1H, J=5.0 Hz), 4.65–4.60 (m, 2H), 4.41 (m, 1H), 4.25–4.15 (m, 2H), 3.75–3.65 (m, 5H), 3.72 (s, 6H), 3.60–3.23 (m, 9H), 2.91–2.80 (m, 1H), 1.38 (d, 3H, J=5.0 Hz).

146 MHz $^{31}P$ NMR ($CDCl_2$) δ11.16 and 10.96 (two peaks due to chiral phosphorous).

Mass spectrum (FAB), m/e, 812, 810, 808. $C_{33}H_{39}Cl_3NO_{14}P$ requires $M^+$ ($^{35}Cl$) 809.

EXAMPLE 4

Etoposide 4'-Thiophosphate Disodium Salt (Compound VIb)

A magnetically stirred suspension of etoposide (2.04 g, 3.47 mmol) in dry acetonitrile (175 mL) was warmed to give a nearly complete solution. The solution was allowed to cool to room temperature and N,N-diisopropylethylamine (2.00 mL, 11.5 mmol) was then added thereto. The mixture was then cooled to 0° C. and thiophosphoryl chloride (0.720 g, 4.17 mmol) was added via syringe over a 30 second period. The mixture was allowed to slowly warm to room temperature over 2–3 hours and stirring continued at room temperature for 16 hours. The mixture was then warmed to 30°–35° C. and kept at that temperature for an additional 4 hours. A major new spot of higher Rf than etoposide was observed by TLC (5% $CH_3OH$ in $CH_2Cl_2$). The reaction mixture was treated with solid sodium bicarbonate (7.4 g) and then deionized $H_2O$ (100 mL) was added. The mixture was stirred at 28°–25° C. for 1.5 hours and at room temperature for 1.5 hours. The mixture was partitioned with deionized $H_2O$ (200 mL), saturated aqueous sodium bicarbonate (30 mL) and ethyl acetate (300 mL). Further workup and reverse phase chromatography was performed according to the procedure delineated in Example 1 to provide 1.03 g (40.8%) of the pure title compound as a colorless solid.

360 MHz $^1H$ NMR ($D_2O$) δ6.93 (s, 1H), 6.60 (s, 1H), 6.27 (s, 2H), 5.93 (d, 2H), 5.09 (d, 1H, J=2.8 Hz), 4.83 (q, 1H, J=5.0 Hz), 4.68 (d, 1H, J=7.8 Hz), 4.63 (d, 1H, J=5.7 Hz), 4.47–4.35 (m, 2H), 4.24 (dd, 1H, J=4.3 and 10.5 Hz), 3.64 (s, 6H), 3.67–3.52 (m, 3H), 3.47–3.29 (m, 3H), 3.17–3.07 (m, 1H), 1.31 (d, 3H, J=5.0 Hz).

Mass spectrum (FAB), m/e 728 ($M^+$), 706 ($M^+$+H–Na). $C_{29}H_{31}Na_2O_{15}PS$ requires $M^+$, 728.

EXAMPLE 5

Etoposide 4'-[[N,N-bis(2-chloroethyl)amino]-[N-(3-hydroxypropyl)aminol]]phosphate (VII, X=O, $R^1$= methyl, $R^6$=H, $R^2$=$R^3$=2-chloroethyl, Y=—NH $(CH_2)_3OH$ A magnetically stirred solution of the compound of Example 3 (280 mg, 0.346 mmol) in $CH_2Cl_2$ (3 ml) was treated with a solution of 3-amino-1-propanol (33.5 mg, 0.446 mmol) in $CH_2Cl_2$ (1 ml). After 5 minutes additional 3-amino-1-propanol (31.0 mg, 0.413 mmol) in absolute methanol (0.5 ml) was added. The reaction mixture was purified by direct application to 4 preparative TLC plates (1 mm, E. Merck silica gel) which were developed using 5–8% $CH_3OH$ in $CH_2Cl_2$. Elution of the desired product band using 5% $CH_3OH$ in ethyl acetate followed by evaporation in vacuo and then further drying at 0.1 torr provided 185 mg (63%) of the pure title compound as a colorless solid (mixture of diastereomers at phosphorus).

360 MHz $^1$H NMR ($CDCl_3$) δ7.20 (br s, 1H), 6.80 (s, 1H), 6.50 and 6.48 (2s, 1H), 6.26 and 6.25 (2s, 2H), 5.97 (d, 2H), 4.88 (m, 1H), 4.73 (q, 1H), 4.64–4.57 (m, 2H), 4.40 (m, 1H), 4.21 –4.13 (m, 2H), 3.71, 3.70 (2s, 6H), 3.71 –3.06 (m, 18H), 2.90–2.80 (m, 1H), 1.37 (d, 3H).

Mass Spectrum (FAB), m/e 849, 851 ($M^+$+H, $^{35}$Cl, $^{37}$Cl). $C_{36}H_{47}Cl_2N_2O_{15}P$ requires $M^+$ 848 ($^{35}$Cl) and 850 ($^{37}$Cl).

EXAMPLE 6

Etoposide 4'-[[N,N-bis(2-chloroethyl)amino]-[N-[2-[(3-nitro-pyridyl-2-yl)disulfide]ethyl]]amino] phosphate (VII, X=O, $R^1$=methyl, $R^6$=H, $R^2$=$R^3$=2-chloroethyl, Y=NH$(CH_2)_2$-SS-(3-nitropyridyl-2-yl)

A mixture of the compound of Example 3 (248 mg, 0.306 mmol) and 2-(3-nitropyridyl)-1-(2-aminoethyl) disulfide hydrochloride (105 mg, 0.393 mmol) was treated with $CH_2Cl_2$ (7 ml) followed by the addition of diisopropylethylamine (100 μl, 0.570 mmol) and dry methanol (0.5 ml). The resulting solution was stirred at room temperature for 1.5 hours and then purified by direct application to four preparative TLC plates (1 mm, E. Merck silica gel) which were developed using 4–5% $CH_3OH$ in ethyl acetate. Elution of the desired product band using 5% $CH_3OH$ in ethyl acetate followed by evaporation in vacuo and then further drying at 0.1 torr provided 231.7 mg (75.3%) of the pure title compound as a yellow-brown solid (mixture of diastereomers at phosphorous).

IR (KBr) 1774, 1598, 1584, 1559, 1509, 1486, 1456, 1421, 1397, 1342, 1236, 1160, 1128, 1096, 1038, 1004, 926, 857, 747, 699 cm$^{-1}$.

360 MHz $^1$H NMR ($CDCl_3$) δ8.81 and 8.77 (2 m, 1H), 8.48 (m, 1H), 7.33 (m, 1H), 6.81 (s, 1H), 6.51 and 6.50 (2s, 1H), 6.26 (br s, 2H), 5.97 (d, 2H), 4.89 (m, 1H), 4.73 (q, 1H), 4.65–4.52 (m, 3H), 4.41 (m, 1H), 4.24–4.14 (m, 2H), 3.71, 3.70 (2s, 6H), 3.71–2.85 (m, 19H), 2.68 (br s, 1H, OH), 2.37 (br s, 1H), OH), 1.37 (d, 3H).

Mass Spectrum (FAB), m/e, 1005, 1007 ($M^+$+H, $^{35}$Cl, $^{37}$Cl). $C_{40}H_{47}Cl_2N_4O_{16}PS_2$ requires $M^+$, 1004 ($^{35}$Cl) and 1006 ($^{37}$Cl).

EXAMPLE 7

Etoposide 4'-diphenyl phosphate ($R^1$=$CH_3$, $R^6$=H, $R^7$=$R^8$=phenyl)

A magnetically stirred suspension of etoposide (10.50 g. 17.84 mmol, dried over $P_2O_5$ at 80° C./0.5 torr) in dry acetonitrile (450 ml) was treated with diisopropylethylamine (4.20 ml, 24.1 mmol) and then diphenyl chlorophosphate (2.00 ml, 9.65 mmol) was added neat via syringe. The mixture was stirred under $N_2$ for two hours at 50° C. at which point all of the etoposide had dissolved. Additional diphenyl chlorophosphate (1.80 ml, 8.68 mmol) was added and the reaction mixture was held at 45° C. for 72 hours. After more of the amine base (0.75 ml, 4.3 mmol) and diphenyl chlorophosphate (0.80 ml, 3.86 mmol) were added, the mixture was stirred at 40°–45° C. for 27 hours, treated with more diphenyl chlorophosphate (0.40 ml, 1.93 mmol), and maintained at 40°–45° C. for 22 hours. Isopropanol (20 ml) was then added, the solvent was evaporated in vacuo, and the solid residue was dissolved in $CH_2Cl_2$ (500 ml), and partitioned with $H_2O$ (400 ml). The aqueous layer was further extracted with $CH_2Cl_2$ (100 ml) and the combined organic extracts were extracted were washed with brine (250 ml) and dried ($Na_2SO_4$/$MgSO_4$). Rotary evaporation followed by flash chromatography on silica gel using 2–3% $CH_3OH$ in $CH_2Cl_2$ provided 12.50 g (85%) of the pure title compound as a colorless solid.

FAB MS m/e (relative intensity) 820 $(M+H)^+$.

IR (KBr) 3460, 2925, 1775, 1601, 1490 cm$^{-1}$.

$^1$H NMR ($CDCl_3$) δ7.28 (m, 8H), 7.15 (m, 2H), 6.78 (s, 1H), 6.47 (s, 1H), 5.95 (m, 2H), 4.85 (d, J=3.5 Hz, 1H), 4.71 (m, 1H), 4.60 (d, J=7.6 Hz, 1H), 4.56 (d, J=5.1 Hz, 1H), 4.38 (m, 1H), 4.22–4.13 (m, 2H), 3.72 . 3.60 (m, 1H), 3.48 (s, 6H), 3.54–3.28 (m, 3H), 3.23 (dd, J=14.2, 5.3 Hz, 1H), 2.78 m, 1H), 1.35 (d, J=5.1 Hz, 3H).

Anal. Calcd. for $C_{41}H_{41}O_{16}P$: C, 60.00; H, 5.04. Found: C, 60.20; H, 5.16.

EXAMPLE 8

Etoposide 4'-phosphate (V; $R^1$=$CH_3$; $R^6$=H, $R^7$=$R^8$=H)

Platinum oxide (0.198 g, 0.87 mmol) from a freshly opened bottle (Aldrich Chemical Co.) was added to a solution of etoposide 4'-diphenyl phosphate (product of Example 7; 0.79 g, 0.962 mmol) in 95 mL of absolute ethanol. The solution was hydrogenated on a Parr apparatus under 45–50 PSI for 4 h at room temperature. The reaction mixture was filtered through a pad of celite using ethanol as eluent. Concentration in vacuo and drying over $P_2O_5$ for 14 h in vacuo provided the desired product as a white solid (0.627, 94%):

FAB MS m/e (relative intensity) 669 $(M+H)^+$

IR (KBr) 3440, 2930, 1778, 1604, 1498 cm$^{-1}$.

$^1$H NMR (DMSO-$d_6$) δ6.93 (s, 1H), 6.46 (s, 1H), 6.12 (s, 2H), 5.94 (m, 2H), 5.17 (bs, 1H), 4.86 (d, J=3.93 Hz, 1H), 4.64 (q, J=7.5, 5.8 Hz, 1H), 4.51–4.42 (m, 2H), 4.20 (d, J=10.7 Hz, 1H), 4.01 (dd, J=12.1, 5.3 Hz, 1H), 3.51 (s, 6H), 3.51–2.75 (m, 7H), 2.83 (m, 1H), 1.16 (d, J=5.1 Hz, 3H).

¯C NMR (DMSO-$d_6$) δ 174.5, 151.2, 151.1, 147.7, 146.2, 126.1, 132.3, 128.8, 109.8, 109.7, 101.5, 101.2, 98.5, 80.0, 74.3, 72.7, 71.7, 67.6, 67.2, 65.7, 55.8, 43.0, 37.1, 20.2, 18.5.

Anal. Calcd. for $C_{29}H_{33}O_{16}P$. 0.85% $H_2O$: C, 50.95; H, 5.11. Found: C, 51.42; H, 4.97.

EXAMPLE 9

Etoposide 4'-bis(2,2,2-trichloroethyl)phosphate (VIII; $R^6$=$CH_3$, $R^1$=H, $R^7$=$R^8$=$CH_2CCl_3$)

The procedure described in Example 7 was repeated using bis(2,2,2-trichloroethyl)chlorophosphate to provide the title compound in 100% yield as a colorless solid following flash chromatography on silica gel.

IR (KRr) 1780, 1610, 1490, 1415, 1345, 1240, 1040, 960, 725 $cm^{-1}$.

300 MHz $^1$NMR ($CDCl_3$) δ 6.81 (s, 1H), 6.49 (s, 1H), 6.27 (s, 2H), 5.98 (dd, 2H), 4.88 (d, 1H, J=3.4 Hz), 4.82–4.70 (m, 5H), 4.64 (d, 1H, J32 7.6 Hz), 4.61 (d, 1H, J=5.3 Hz), 4.41 (dd, 1H), 4.25–4.13 (m, 2H), 3.75 (m, 1H), 3.73 (s, 6H), 3.56 (m, 1H), 3.43 (dd, 1H), 3.34–3.24 (m, 3H), 2.91–2.82 (m, 1H), 1.38 (d, 3H, J=4.9 Hz).

Mass Spectrum (FAB), m/e=928.9848 ($M^+$+H). $C_{33}H_{36}Cl_6O_{16}P$ requires 928.9872.

EXAMPLE 10

Etoposide 4'-phosphate disodium salt from etoposide 4'-phosphate

Method A

Commercial Dowex 50×8–100 cation exchange resin in the hydrogen form (20 g, Aldrich Chemical Co.) was treated with excess 1N NaOH. The resulting resin in Na+ form was packed into a 2 cm column and equilibrated with water. Etoposide 4'-phosphate (product of Example 8, 1.25 g, 1.87 mmol) dissolved in 25 ml of deionized water was applied to the top of the packed column and the column was eluted with water. Fractions containing the title compound were pooled, filtered, and lyophilized to yield 1.15 g of the title compound as a white and fluffy material.

Method B

To 2.90 g (4.34 mmol) of crude etoposide 4'-phosphate (product of Example 8) was added deionized water (50 ml) and sodium bicarbonate (3.00 g, 35.7 mmol). The mixture was stirred at room temperature for 30 minutes during which time $CO_2$ evolution ceased. The mixture was then chromatographed as described in Example 1. Elution with deionized water (300 ml) and then 4:1 $H_2O/CH_3OH$ provided 1.90 g (61%) of pure title compound as a fluffy white solid following lyophilization.

EXAMPLE 11

The general procedure described in Example 2 is repeated with the exception that the diethylamine used therein is replaced by the amines listed below to provide the corresponding etoposide 4'-phosphorodiamidates.

| | Compound VII (X = O, $R^1$ = methyl, $R^6$ = H, Y = $NR^2R^3$) | |
|---|---|---|
| Amine | $R^2$ | $R^3$ |
| propylamine | H | $CH_2CH_2CH_3$ |
| ethanolamine | H | $CH_2CH_2OH$ |
| methoxyethylamine | H | $CH_2CH_2OCH_3$ |
| N-acetylethylenediamine | H | $CH_2CHNC(O)CH_3$ |
| 2-methylallylamine | H | $CH_2CH(CH_3)=CH_2$ |
| allylamine | H | $CH_2CH=CH_2$ |
| dimethylaminopropylamine | H | $(CH_2)N(CH_3)_2$ |
| N-methylethylenediamine | H | $CH_2CH_2NCH_3$ |
| trifluoroethylamine | H | $CH_2CF_3$ |
| 2-aminoethanethiol | H | $CH_2CH_2SH$ |
| cyclohexylamine | H | cyclohexyl |
| 2-amino-1-methoxypropane | H | $CH(CH_3)CH_2OCH_3$ |

-continued

| | Compound VII (X = O, $R^1$ = methyl, $R^6$ = H, Y = $NR^2R^3$) | |
|---|---|---|
| Amine | $R^2$ | $R^3$ |
| 2-(ethylthio)-ethylamine | H | $CH_2CH_2SCH_2CH_3$ |
| chloroethylamine | H | $CH_2CH_2Cl$ |
| 4-aminocyclohexanol | H | |
| ethylmethylamine | $CH_3$ | $CH_2CH_3$ |
| ethylbutylamine | $CH_2CH_3$ | $(CH_2)_3CH_3$ |
| methylaminoethanol | $CH_3$ | $CH_2CH_2OH$ |
| bis(2-chloroethyl)amine | $CH_2CH_2Cl$ | $CH_2CH_2Cl$ |
| 2-propylaminoethanol | $CH_2CH_2CH_3$ | $CH_2CH_2OH$ |
| 3-methylaminopropionitrile | $CH_3$ | $CH_2CH_2CN$ |
| piperidine | $R^2 + R^3$ = | $—(CH_2)_3—$ |

EXAMPLE 12

The general procedure described in Example 3 is repeated with the exception that the bis(2-chloroethyl)amine used there is replaced by the amines listed below to provide the corresponding etoposide chlorophoroamidates.

| | Compound VII (X = O, $R^1$ = methyl, $R^6$ = H, Y = Cl) | |
|---|---|---|
| Amine | $R^2$ | $R^3$ |
| propylamine | H | $CH_2CH_2CH_3$ |
| ethanolamine | H | $CH_2CH_2OH$ |
| methoxyethylamine | H | $CH_2CH_2OCH_3$ |
| N-acetylethylenediamine | H | $CH_2CHNC(O)CH_3$ |
| 2-methylallylamine | H | $CH_2CH(CH_3)=CH_2$ |
| allylamine | H | $CH_2CH=CH_2$ |
| dimethylaminopropylamine | H | $(CH_2)N(CH_3)_2$ |
| N-methylethylenediamine | H | $CH_2CH_2NCH_3$ |
| Trifluoroethylamine | H | $CH_2CF_3$ |
| 2-aminoethanethiol | H | $CH_2CH_2SH$ |
| cyclohexylamine | H | cyclohexyl |
| 2-amino-1-methoxypropane | H | $CH(CH_3)CH_2OCH_3$ |
| 2-(ethylthio)-ethylamine | H | $CH_2CH_2SCH_2CH_3$ |
| chlorethylamine | H | $CH_2CH_2Cl$ |
| 4-aminocyclohexanol | H | 4-OH cyclohexyl |
| ethylmethylamine | $CH_3$ | $CH_2CH_3$ |
| ethylbutylamine | $CH_2CH_3$ | $(CH_2)_3CH_3$ |
| methylaminoethanol | $CH_3$ | $CH_2CH_2OH$ |
| diethylamine | $CH_2CH_3$ | $CH_2CH_3$ |
| 2-propylaminoethanol | $CH_2CH_2CH_3$ | $CH_2CH_2OH$ |
| 3-methylaminopropionitrile | $CH_3$ | $CH_2CH_2CN$ |
| piperidine | $R^2 + R^3$ = | $—(CH_2)_5—$ |

EXAMPLE 13

The general procedure in Example 5 is repeated with the exception that the 3-aminopropanol used therein is replaced by the following amines to provide the corresponding unsymmetrical etoposide phosphorodiamidates.

| | Compound VII (X = O, $R^1$ = methyl, $R^6$ = H, Y = $NR^4R^5$, $R^2$ = $R^3$ = $CH_2CH_2Cl$) | |
|---|---|---|
| Amine | $R^4$ | $R^5$ |
| propylamine | H | $CH_2CH_2CH_3$ |
| ethanolamine | H | $CH_2CH_2OH$ |
| methoxyethylamine | H | $CH_2CH_2OCH_3$ |
| N-acetylethylenediamine | H | $CH_2CHNC(O)CH_3$ |
| 2-methylallylamine | H | $CH_2CH(CH_3)=CH_2$ |

-continued

| Amine | Compound VII (X = O, $R^1$ = methyl, $R^6$ = H, Y = $NR^4R^5$, $R^2$ = $R^3$ = $CH_2CH_2Cl$) $R^4$ | $R^5$ |
|---|---|---|
| allylamine | H | $CH_2CH{=}CH_2$ |
| dimethylaminopropylamine | H | $(CH_2)N(CH_3)_2$ |
| N-methylethylenediamine | H | $CH_2CH_2NCH_3$ |
| Trifluoroethylamine | H | $CH_2CF_3$ |
| 2-aminoethanethiol | H | $CH_2CH_2SH$ |
| cyclohexylamine | H | cyclohexyl |
| 2-amino-1-methoxypropane | H | $CH(CH_3)CH_2OCH_3$ |
| 2-(ethylthio)-ethylamine | H | $CH_2CH_2SCH_2CH_3$ |
| chlorethylamine | H | $CH_2CH_2Cl$ |
| 4-aminocyclohexanol | H | 4-OH cyclohexyl |
| ethylmethylamine | $CH_3$ | $CH_2CH_3$ |
| ethylbutylamine | $CH_2CH_3$ | $(CH_2)_3CH_3$ |
| methylaminoethanol | $CH_3$ | $CH_2CH_2OH$ |
| bis(2-chloroethyl)amine | $CH_2CH_3$ | $CH_2CH_2Cl$ |
| 2-propylaminoethanol | $CH_2CH_2CH_3$ | $CH_2CH_2OH$ |
| 3-methylaminopropionitrile | $CH_3$ | $CH_2CH_2CN$ |
| piperidine | $R^2 + R^3$ = | $—(CH_2)_5—$ |

EXAMPLE 14

The general procedure described in Example 7 is repeated with the exception that the diphenyl chlorophosphate used therein is replaced with the chlorophosphates listed below to provide the corresponding etoposide 4'-phosphate diesters (X=O, $R^1$=methyl, $R^6$=H, $R^7$=$R^8$=R described below).

| chlorophosphates [$(RO)_2P(O)Cl$] |
|---|
| R = methyl |
| ethyl |
| benzyl |
| p-nitrobenzyl |
| p-nitrophenyl |
| p-bromobenzyl |
| p-nitrophenethyl |
| cyanoethyl |
| o-(t-butyl)phenyl |

EXAMPLE 15

The general procedures described in Examples 1 to 14 are repeated with the exception that the etoposide starting materials used therein are replaced with the corresponding teniposide compounds to provide the corresponding teniposide products.

What is claimed is:

1. A compound having the formula

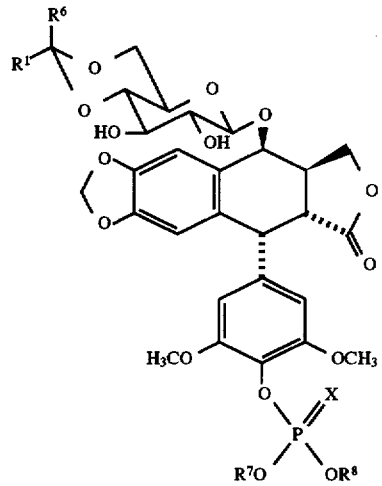

V wherein $R^6$ is H and $R^1$ is selected from the group consisting of $(C_{1-10})$alkyl; $(C_{2-10})$alkenyl; $(C_{5-6})$cycloalkyl; 2-furyl; 2-thienyl; $(C_{6-10})$aryl; $(C_{7-14})$aralkyl; and $(C_{8-14})$aralkenyl wherein each of the aromatic rings may be unsubstituted or substituted with one or more groups selected from halo, $(C_{1-8})$alkyl, $(C_{1-8})$alkoxy, hydroxy, nitro, and amino; or $R^1$ and $R^6$ are each $(C_{1-8})$alkyl; or $R^1$ and $R^6$ and the carbon to which they are attached join to form a $(C_{5-6})$cycloalkyl group;

X is oxygen or sulfur;

$R^7$ $R^8$ are independently selected from the group consisting of H, $(C_{1-5})$alkyl, halo-substituted $(C_{1-5})$alkyl, cyano-substituted $(C_{1-5})$alkyl, $(C_{3-6})$cycloalkyl, $(C_{6-10})$aryl, $(C_{7-14})$aralkyl, wherein the ring portion of said aryl and aralkyl groups is unsubstituted or substituted with a group selected from the group consisting of alkyl, halo, and nitro;

or a pharmaceutically acceptable salt thereof.

2. The compound of claim 1 having the formula

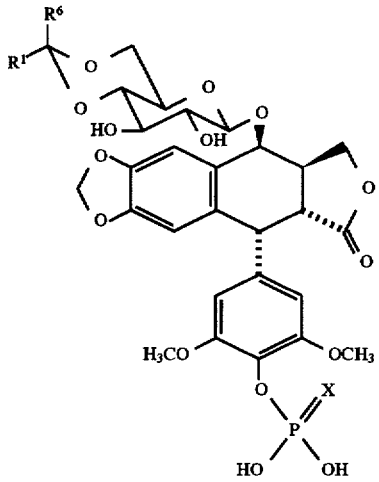

wherein $R^1$, $R^6$ and X are as defined in claim 1; or a pharmaceutically acceptable salt thereof.

3. The compound of claim 1 wherein $R^6$ is H and $R^1$ is methyl or 2-thienyl.

4. The compound of claim 2 wherein $R^6$ is H and $R^1$ is methyl or 2-thienyl.

5. The compound of claim 2 wherein $R^6$ is H and $R^1$ is methyl.

6. The compound of claim 5 wherein X is oxygen.

7. The compound of claim 5 wherein X is sulfur.

8. The compound of claim 2 wherein the pharmaceutically acceptable salt is the sodium salt.

9. The compound etoposide 4'-phosphate disodium salt.

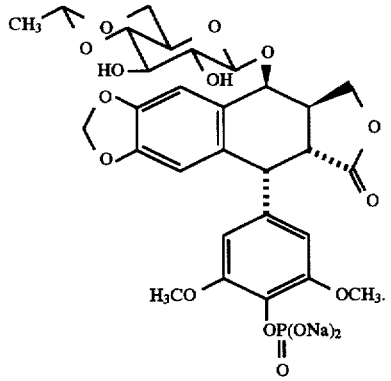

10. The compound etoposide 4'-thiophosphate disodium salt.

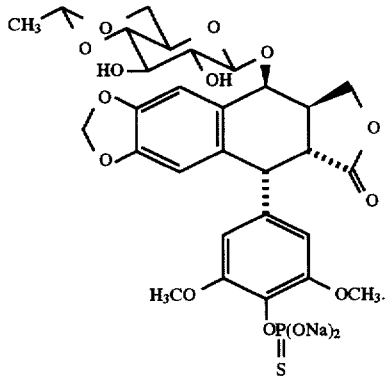

11. The compound of claim 1 wherein $R^7$ and $R^8$ are the same and are selected from the group consisting of $(C_{1-5})$ alkyl; halo-substituted $(C_{1-5})$alkyl; cyano-substituted $(C_{1-5})$ alkyl; $(C_{6-10})$aryl; and $(C_{7-14})$aralkyl; wherein the ring portion of said aryl and aralkyl groups is unsubstituted or substituted with a group selected from alkyl, halo, and nitro.

12. The compound of claim 11 wherein $R^6$ is H and $R^1$ is methyl or 2-thienyl.

13. The compound of claim 12 wherein $R^1$ is methyl.

14. The compound of claim 13 wherein X is oxygen.

15. The compound of claim 14 wherein $R^7$ and $R^8$ are each phenyl.

16. The compound of claim 14 wherein $R^7$ and $R^8$ are each 2,2,2-trichloroethyl.

17. The compound having the formula

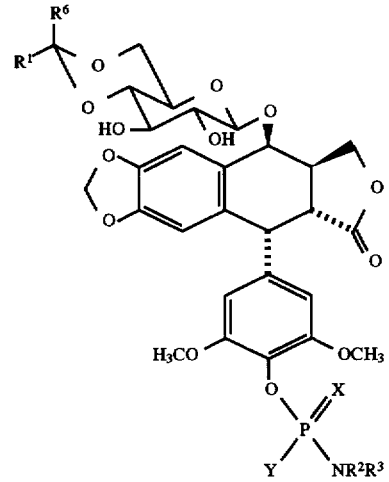

wherein $R^1$, $R^6$ and X are as defined in claim 1; Y is Cl, OH, or $NR^4R^5$; $R^2$, $R^3$, $R^4$, and $R^5$ are each independently selected from the group consisting of H, $(C_{1-5})$alkyl, $(C_{2-5})$ alkenyl, $(C_{3-6})$cycloalkyl; wherein said alkyl, alkenyl, cycloalkyl may be unsubstituted or substituted with one or more of a group selected from the group consisting of hydroxy, alkoxy, halo, mercapto, cyano, alkylthio, alkanoylamino, dialkylamino, alkylamino, and nitropyridyl disulfide, or $R^2$, $R^3$, and the nitrogen to which they are attached together represent a 3 to 6 membered ring; or $R^4$, $R^5$, and the nitrogen to which they are attached together represent a 3 to 6 membered ring; or a pharmaceutically acceptable salt thereof, *provided that when $R_1$ is methyl, $R_6$ is H, and $R^2$ and $R^3$ are each 2-chloroethyl, Y is not $NR^4R^5$ where $R^4$ is H and $R^5$ is either 3-hydroxypropyl or*

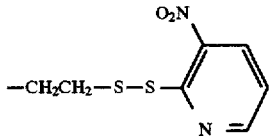

18. The compound of claim 17 wherein $R^6$ is H: $R^1$ is methyl or 2-thienyl; Y is Cl or $NR^4R^5$; X is oxygen or sulfur, and $R^2$, $R^3$, $R^4$ and $R^5$ are independently selected from the group consisting of H, $(C_{1-5})$ alkyl, halo substituted $(C_{1-5})$ alkyl, hydroxy substituted $(C_{1-5})$ alkyl, and nitropyridyl disulfide substituted $(C_{1-5})$ alkyl.

19. The compound of claim 18 wherein X is oxygen.

20. The compound of claim 19 wherein $R^1$ is methyl.

21. The compound of claim 20 wherein $R^2$ and $R^3$ are each 2-chloroethyl; and Y is Cl.

22. The compound of claim 20 wherein Y is $NR^4R^5$.

23. The compound of claim 22 wherein $R^2$, $R^3$, $R^4$, and $R^5$ are each ethyl.

[24. The compound of claim 22 wherein $R^2$ and $R^3$ are each 2-chloroethyl; $R^4$ is H; and $R^5$ is 3-hydroxypropyl.]

[25. The compound of claim 22 wherein $R^2$ and $R^3$ are each 2-chloroethyl; $R^4$ is H; and $R^5$ is ]

26. An intermediate having the formula

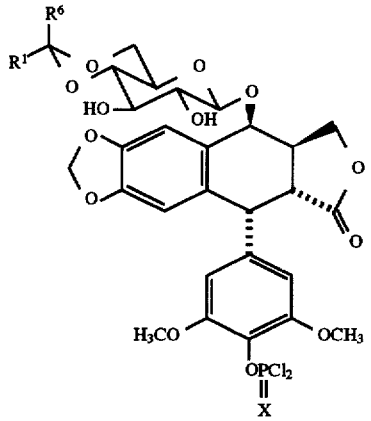

wherein $R^1$, $R^6$, and X are as defined in claim 1.

27. The compound of claim 26 wherein $R^6$ is H; $R^1$ methyl; and X is oxygen.

28. The compound of claim 26 wherein $R^6$ is H; $R^1$ is methyl; and X is sulfur.

29. A pharmaceutical composition which comprises an antitumor effective amount of a compound of claim 1 or claim 17, and a pharmaceutically acceptable carrier.

30. A composition according to claim 29 wherein said compound is etoposide 4'-phosphate disodium salt.

31. A process for preparing a compound of the formula

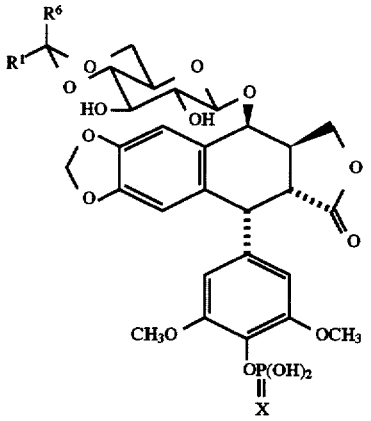

wherein $R^1$, $R^6$, and X are as defined in claim 1 or a pharmaceutically acceptable salt thereof which comprises the steps of:

(a) reacting a compound of formula IX

IX

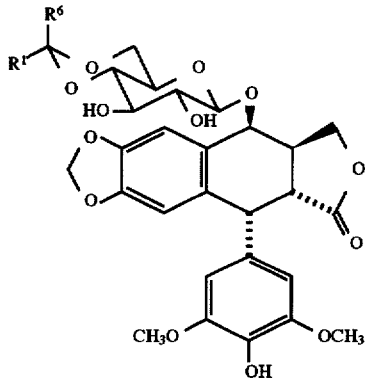

with a compound of the formula Hal-P(X)(O–G)$_2$, wherein Hal is a halogen, G is a phosphate protecting group, and $R_1$, $R_6$, and X are as defined in claim 1, in acetonitrile or ($C_{2-5}$)CN and in the presence of a trialkylamine to form a compound of formula X

X

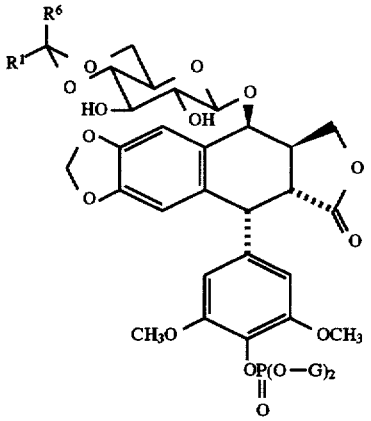

and (b) removing the phosphate protecting group.

* * * * *

UNITED STATES PATENT AND TRADEMARK OFFICE

(12) CERTIFICATE EXTENDING PATENT TERM
UNDER 35 U.S.C. § 156

| | | | |
|---|---|---|---|
| (68) | PATENT NO. | : | RE. 35,524 |
| (45) | REISSUED | : | February 27, 1990 |
| (75) | INVENTOR(S) | : | Mark G. Saulnier, et al. |
| (73) | PATENT OWNER | : | Bristol-Myers Squibb Company |
| (95) | PRODUCT | : | ETOPOPHOS® (etoposide phosphate) |

This is to certify that an application under 35 U.S.C. § 156 has been filed in the United States Patent and Trademark Office, requesting extension of the term of U.S. Patent No. RE. 35,524 based upon the regulatory review of the product ETOPOPHOS® (etoposide phosphate) by the Food and Drug Administration. Since it appears that the requirements of the law have been met, this certificate extends the term of the patent for the period of

(94) 1,017 days from August 4, 2007, the original expiration date of the patent, subject to the payment of maintenance fees as provided by law, with all rights pertaining thereto as provided by 35 U.S.C. § 156(b).

I have caused the seal of the Patent and Trademark Office to be affixed this 18th day of July 2001.

Nicholas P. Godici

Nicholas P. Godici
Acting Under Secretary of Commerce for Intellectual Property and
Acting Director of the United States Patent and Trademark Office